US010750996B2

(12) United States Patent
Wariar

(10) Patent No.: US 10,750,996 B2
(45) Date of Patent: Aug. 25, 2020

(54) MULTI-SENSOR BODY FLUID VOLUME INDEX

(71) Applicant: Cardiac Pacemakers, Inc., St. Paul, MN (US)

(72) Inventor: Ramesh Wariar, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 756 days.

(21) Appl. No.: 15/163,175

(22) Filed: May 24, 2016

(65) Prior Publication Data

US 2016/0354032 A1 Dec. 8, 2016

Related U.S. Application Data

(60) Provisional application No. 62/169,909, filed on Jun. 2, 2015.

(51) Int. Cl.
*A61B 5/00* (2006.01)
*A61B 5/08* (2006.01)
(Continued)

(52) U.S. Cl.
CPC ............ *A61B 5/4836* (2013.01); *A61B 5/053* (2013.01); *A61B 5/0538* (2013.01);
(Continued)

(58) Field of Classification Search
CPC ..... A61B 5/053; A61B 5/0538; A61B 5/0816; A61B 5/091; A61B 5/14546;
(Continued)

(56) References Cited

U.S. PATENT DOCUMENTS 6,076,015 A 6/2000 Hartley et al.
7,743,151 B2 6/2010 Vallapureddy et al.
(Continued)

FOREIGN PATENT DOCUMENTS

WO WO-2016196080 A1 12/2016

OTHER PUBLICATIONS

"Definition of Hypovolemia". https://www.medicinenet.com/script/main/art.asp?articlekey=3871 Retrieved Sep. 12, 2018.*
(Continued)

*Primary Examiner* — Christopher Koharski
*Assistant Examiner* — James Moss
(74) *Attorney, Agent, or Firm* — Schwegman Lundberg & Woessner, P.A.

(57) ABSTRACT

An apparatus comprises plurality of physiologic sensors and a processor circuit. The sensors provide sensor signals having physiological information and include a heart sound sensor and an impedance sensor. The processor circuit includes a volume index module configured to determine a value of at least one heart sound parameter using the heart sound signal and determine a value of at least one physiological impedance parameter value using the impedance signal, calculate a volume index representative of fluid volume status of the subject using the at least one heart sound parameter value and the at least one physiological impedance parameter value, compare a determined metric of the calculated volume index to one or more high threshold metric values and one or more low threshold metric values, and generate an indication of a fluid volume status of the subject according to the comparison.

16 Claims, 5 Drawing Sheets

(51) Int. Cl.
| | |
|---|---|
| *A61B 5/053* | (2006.01) |
| *A61B 7/00* | (2006.01) |
| *A61B 5/091* | (2006.01) |
| *A61B 5/145* | (2006.01) |
| *A61B 7/02* | (2006.01) |
| *A61M 5/172* | (2006.01) |
| *A61N 1/365* | (2006.01) |
| *A61N 1/39* | (2006.01) |
| *A61M 5/142* | (2006.01) |

(52) U.S. Cl.
CPC ............ *A61B 5/0816* (2013.01); *A61B 5/091* (2013.01); *A61B 5/14546* (2013.01); *A61B 5/4839* (2013.01); *A61B 5/4875* (2013.01); *A61B 5/686* (2013.01); *A61B 5/7278* (2013.01); *A61B 7/00* (2013.01); *A61B 7/02* (2013.01); *A61M 5/1723* (2013.01); *A61N 1/36585* (2013.01); *A61N 1/3987* (2013.01); *A61M 5/14276* (2013.01); *A61M 2205/04* (2013.01)

(58) Field of Classification Search
CPC ..... A61B 5/4836; A61B 5/4875; A61B 5/686; A61B 5/7278; A61B 7/00; A61B 7/02; A61M 5/14276; A61M 5/1723; A61M 2205/04; A61N 1/36585; A61N 1/3987
USPC .................................................. 600/300, 301
See application file for complete search history.

(56) References Cited

U.S. PATENT DOCUMENTS

| | | | |
|---|---|---|---|
| 7,972,275 B2 | 7/2011 | Siejko et al. | |
| 8,818,505 B2 | 8/2014 | Bhunia et al. | |
| 2005/0080460 A1 | 4/2005 | Wang et al. | |
| 2006/0258952 A1 | 11/2006 | Stahmann et al. | |
| 2008/0288030 A1* | 11/2008 | Zhang .................. | A61B 5/4869 607/62 |
| 2012/0165884 A1 | 6/2012 | Xi et al. | |
| 2014/0378849 A1 | 12/2014 | Krimsky et al. | |

OTHER PUBLICATIONS

"Definition of Hypervolemia". https://www.medicinenet.com/script/main/art.asp?articlekey=32171 Retrieved Sep. 12, 2018.*

Alrawi, Sadir J., et al., "Correlation of blood volume values and pulmonary artery catheter measurementa", Saudi Med J, vol. 23 (11), (2002), 1367-1372.

Katz, Stuart D., "In Search of Euvolemia in Heart Failure", JACC Heart Failure, vol. 2 No. 3, Editorial Comment, (2014), 2 pgs.

Seyedi, Mirhojjat, et al., "A Survey on Intrabody Communications for Body Area Network Applications", IEEE Transactions on Biomedical Engineering, vol. 60, No. 8, (Aug. 2013), 13 pgs.

"International Application Serial No. PCT/US2016/033909, International Preliminary Report on Patentability dated Dec. 14, 2017", 8 pgs.

"International Application Serial No. PCT/US2016/033909, International Search Report dated Aug. 29, 2016", 4 pgs.

"International Application Serial No. PCT/US2016/033909, Written Opinion dated Aug. 29, 2016", 7 pgs.

Ana, Silvia Androne, et al., "Relation of unrecognized hypervolemia in chronic heart failure to clinical status, hemodynamics, and patient outcomes", American Journal of Cardiology.,vol. 93, No. 10, May 1, 2004 (May 1, 2004), XP055296354,US, (May 1, 2004), 1254-1259.

\* cited by examiner

MULTI-SENSOR BODY FLUID VOLUME INDEX

CLAIM OF PRIORITY

This application claims the benefit of priority under 35 U.S.C. § 119(e) of U.S. Provisional Patent Application Ser. No. 62/169,909, filed on Jun. 2, 2015, which is herein incorporated by reference in its entirety.

BACKGROUND

The regulation of body fluid volume and its composition is essential for human life. Several diseases (particularly of the heart, liver, and kidney) disturb volume balance and are associated with an expansion of fluid contained in the extracellular and vascular spaces of the body. An expanded volume state often (but not always) manifests as clinical symptoms of breathlessness (dyspnea) and swelling (edema). Symptoms of congestion lead to millions of hospitalizations worldwide in patients with heart failure (HF) and are associated with significantly worse patient outcomes. Thus, continuous monitoring and optimization of volume status using ambulatory devices may allow reduction of patient morbidity and mortality as well as healthcare utilization and cost.

Ambulatory medical devices include implantable medical devices (IMDs), wearable medical devices, and handheld medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. Other examples of IMDs include implantable drug delivery systems, implantable devices with neural stimulation capability (e.g., vagus nerve stimulator, carotid sinus stimulator, spinal cord stimulator, deep brain stimulator, etc.), and cardiac assist devices. These devices are used to treat patients using electrical or other therapy, or to aid a physician or caregiver in patient diagnosis through internal monitoring of a patient's condition.

Some implantable medical devices can be diagnostic-only devices, such as implantable loop recorders (ILRs) and subcutaneously implantable heart failure monitors (SubQ HFMs). Subcutaneously implantable devices may include a variety of different sensors to monitor one or more internal patient parameters such as electrodes that are able to sense cardiac signals without being in direct contact with the patient's heart, body impedance to detect fluid, motion sensors to sense acceleration and cardiac vibrations, acoustic sensors to measure tissue properties, thermal sensors, and chemosensors to sense the biochemical composition of body fluids.

Some examples of wearable medical devices include wearable cardioverter defibrillators (WCDs) and wearable diagnostic devices (e.g., an ambulatory monitoring vest). WCDs can be monitoring devices that include surface electrodes. The surface electrodes may be arranged to provide one or both of monitoring to provide surface electrocardiograms (ECGs) and delivery of cardioverter and defibrillator shock therapy. A wearable medical device can also include a monitoring patch worn by the patient such as an adherable patch or can be included with an article of clothing worn by the patient.

Monitoring volume status of patients can be challenging. Radioisotope indicator dilution is the gold standard for volume measurement, but is is not feasible for routine clinical or ambulatory monitoring. Methods in clinical use include a variety of biomarkers derived from physical examination (for edema, jugular venous distension, auscultation, orthostatic vital signs), chest radiography, echocardiography, and blood chemistry. While some measures such as physical assessments and chest radiography are not sensitive or specific to volume status, others are not feasible for repeated serial measurements needed for therapy adjustment. Implanted diagnostic-only devices that measure left atrial pressure (LAP) or pulmonary artery pressure (PAP) have been recently available for HF patients.

However these devices require a dedicated implant in the heart or circulatory system of the patient exposing the patient to greater risk of adverse events. A more desirable alternative would be the measurement of a volume status indicator that employ less invasive sensors, or sensors already available in implanted CFM devices. Due to individual sensor limitations, it has not been possible to derive a reliable volume index to date that can be used to optimize patient therapy. A volume index derived from multiple sensor measurements such as heart sounds, impedance, systolic time intervals and respiration with adjustments for patient age, body mass index, cardiac disease and comorbidities overcomes limitations associated with any one sensor or methodology.

OVERVIEW

Ambulatory medical devices can sense physiologic indicators of a patient. This provides for constant or near-constant monitoring of the patient's condition. The present subject matter relates to transforming physiologic sensor parameters available in ambulatory devices into a patient's fluid volume status.

An apparatus example includes a plurality of physiologic sensors and a processor circuit. The sensors include a heart sound sensor configured to generate a heart sound signal representative of mechanical cardiac activation of a subject and an impedance sensor configured to generate an impedance signal representative of physiological impedance of the subject. The processor circuit includes a volume index module configured to determine a value of at least one heart sound parameter using the heart sound signal and determine a value of at least one physiological impedance parameter value using the impedance signal, calculate a volume index representative of fluid volume status of the subject using the at least one heart sound parameter value and the at least one physiological impedance parameter value, compare a determined metric of the calculated volume index to one or more high threshold metric values and one or more low threshold metric values, and generate an indication of a fluid volume status of the subject according to the comparison. The volume index calculated by the device is used to control one or more therapies to ensure the patient is maintained within an optivolemic range.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may

DETAILED DESCRIPTION

Figure 1:
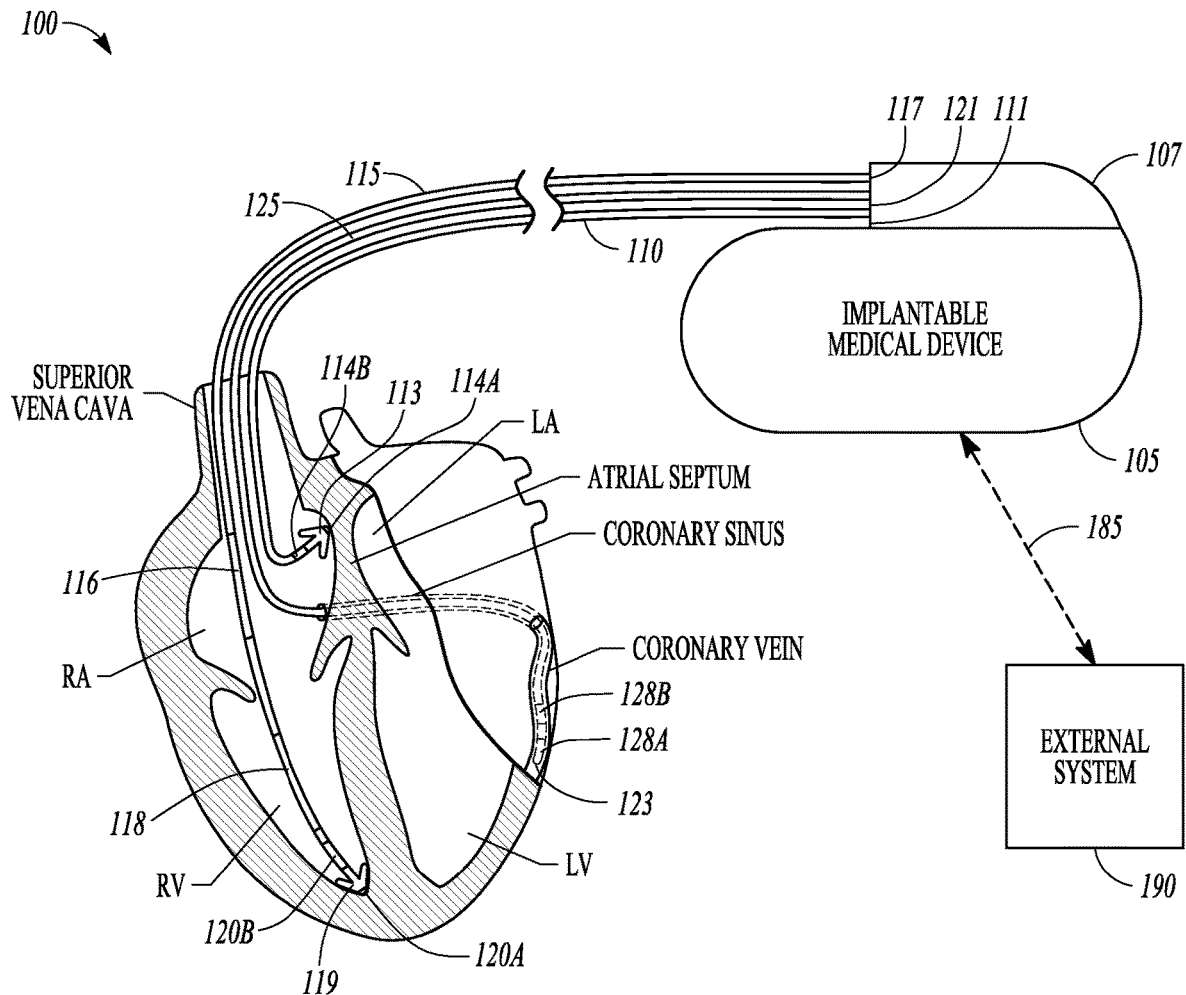
FIG. 1 is an illustration of portions of a system that uses an IMD.

Water is a major constituent of the body and comprises about 60% of body weight. One third of total body water is contained in the extracellular space (extracellular fluid, or ECF). Three fourths of the ECF is made up of interstitial fluid (ISF) and the remainder is contained in the vascular space (as blood plasma). Within the vascular space, 85% of blood circulates in the venules and veins, and the remainder in arteries and arterioles. ECF osmolarity is one of the major forces responsible for movement of water between the vascular and interstitial spaces. ECF osmolality is determined predominantly by sodium chloride (NaCl). Changes in hydrostatic and osmolar forces (the Starling forces) across blood capillaries determine the flow of fluid between the vascular and interstitial spaces. Any excess ISF is returned to the vascular compartment via the lymphatics. Because changes in total body volume impact circulatory hemodynamics and normal functioning of tissues, the body keeps extracellular and total body water within normal limits (referred to as euvolemia) by sending signals to the kidney to adjust the excretion of salt and water.

The ECF is thought to be sensed via the effective arterial blood volume (EABV). The EABV is not a measurable or distinct body compartment but reflects the filling of the arterial tree as well as tissue perfusion. In a healthy state, the EABV is believed to vary with the extracellular volume (ECV). The relationship between EABV and ECV is disturbed in pathologic states causing the body to retain fluid despite increased ECV. The EABV is believed to be sensed by distributed receptors located in the cardiac atria and ventricles, pulmonary vasculature, carotid sinus, aortic arch, renal juxtaglomerular apparatus, central nervous system, and liver. The signals to restore volume status have the capacity to increase as well as decrease the renal excretion of salt and water. The major systems involved are the central nervous system and renal sympathetic nerves, renin-angiotensin-aldosterone system, arginine vasopressin, and natriuretic peptides. The relation of these hormones to volume status enables some of them, like natriuretic peptides, to be used as biomarkers of increased fluid.

A variety of different diseases lead to an abnormal expansion of ECV (referred to as hypervolemia). In patients with systolic HF, the reduction in cardiac output is sensed by the body as a reduction in EABV. In other cases where cardiac output is normal or increased, a decrease in EABV results because of relaxation of arterial blood vessels. Nephrotic syndromes (a disease of the kidneys) can lead to the loss of large quantities of protein into the urine and disturbs the osmotic balance across the capillaries and leads to a flow of water from the vascular to the interstitial space, thereby reducing EABV. In hepatic cirrhosis, EABV is decreased by the pooling of blood in the splanchnic venous system.

The clinical assessment of volume status is difficult and challenging particularly in a chronic illness like HF. Alternatives include physical examination, orthostatic vital signs, auscultation, acoustic cardiography, chest radiography, natriuretic peptides, pulmonary artery pressure, bioimpedance, and thoracic ultrasonography. In addition to measurement, the determination of optimal volume status is not obvious when volume control mechanisms of the body are disturbed. Errors in volume assessment (as well as the volume targeted with treatment) can lead to withholding of needed therapy or administration of unneeded therapy both of which could lead to increased patient morbidity and mortality.

Volume status measured by implanted medical devices may be used to treat these different disease conditions. Hypervolemia in HF patients can be treated using pharmacologic therapies such as diuretics or vasodilators, as well as device therapies such as cardiac resynchronization therapy or extracorporeal ultrafiltration. These therapies have to be monitored and controlled to ensure that the patient is kept in an optimal volume range. Therefore, a useful volume index will have at least two thresholds to represent hypo- and hypervolemia. The range between the two thresholds reflects the optivolemic or "ideal volume" state for a given patient which is used as a goal for volume restoration therapies. If additional grades of hypo- and hypervolemia are needed (for example, moderate or severe hypervolemia) multiple thresholds may be used below or above the optivolemic range. Early attention to signs of worsening HF such as hypervolemia is helpful in providing optimal treatments to patients. In patients on renal dialysis, the optivolemic range may be used to adjust the fluid removal goals during dialysis to bring patients to their "dry weight" without episodes of hemodynamic instability. In patients with liver cirrhosis, volume status may be managed using a combination of diuretics and dietary restriction (such as sodium restriction), as well as paracentesis and intrahepatic portosystemic shunts to treat refractory ascites.

A variety of different hormones that are secreted by the body in response to increased circulating blood volume may be used as biomarkers of fluid volume status. One class of biomarkers is natriuretic peptides (NP). NPs are released from heart muscle in response to excessive stretch and include atrial natriuretic peptide (ANP), B-type Naturetic Peptide (BNP) or its prohormone, NT-proBNP. BNP typically increases with left ventricular dysfunction and in patients having worsening heart failure. Thus, NPs can be used to screen for HF, but more importantly, serial measurements of NPs can be used to optimize patient therapy. In addition to NT-proBNP and BNP, other more effective circulating biomarkers are being developed. The mid-region of the pro-peptide for ANP (MR-proANP) is a natriuretic peptide that adds additional prognostic information to NT-proBNP. Soluble ST2 (sST2) and its transmembrane ligand ST2L is generated from the ST2 gene expressed by cardiac muscle in response to myocardial strain. Although these new circulating biomarkers add significant diagnostic and prognostic value to HF management, they require multiple blood draws for serial measurements and tens of minutes of processing time before results can be obtained.

In contrast, if a reliable volume index can be derived from device-based sensors, it would provide constant monitoring of the fluid volume status and possibly reduce the number of clinical visits and delays in monitoring patients. Because a wide distribution of acceptable ECV exists across patients, continuous ambulatory volume measures can provide the ability to tailor therapies to specific patients based upon their unique volume changes measured continuously throughout the day and night. Continuous monitoring enables multiple measurements made across different times of day, patient posture, and activities of daily living from which small sub-clinical changes can be detected. Monitoring pulmonary arterial (PA) pressure can provide a measure of fluid status and has been shown to reduce hospitalizations for patients with HF. However, PA pressure monitoring requires a dedicated monitoring implant in the vasculature of the patient which carries risks of infection and thromboembolism. Further, single sensor pressure measurements, like other independent biomarkers are not always correlated with volume status. A more desirable method would be to estimate volume status using multiple available sensors in implanted CFM devices or other ambulatory medical devices.

Patients with fluid volume overload are sometimes prescribed diuretic drug therapy or vasodilating drug therapy to treat fluid volume overload. In addition, HF patients are sometimes prescribed an ambulatory medical device (e.g., an IMD) that provides therapy, such as the drug therapy to directly treat the fluid volume overload or CRT to improve heart function.

FIG. 1 is an illustration of portions of a system 100 that uses an IMD 105. Examples of the IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMB programmer or other external system 190 that communicates one or more wireless signals 185 with the IMB 105, such as by using radio frequency (RF) or by one or more other telemetry methods.

The example shown includes a right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV electrodes 120A and 120B, or an electrode formed on the can of IMD 105, allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

As explained previously herein, the ambulatory medical device such as the IMD shown in the example of FIG. 1 can provide electrogram sensing. The device may be configured to sense other types of physiological signals, such as sense signals representative of physiological impedance. For instance, an electrical current could be applied between an RV electrode (e.g., RV electrode 120B) and an electrode formed on the device can. Voltage resulting from the applied current can be measured using another RV electrode (e.g., electrode 118) and an electrode formed on the device header 107. Impedance across at least a portion of the thorax region of the subject may then be calculated using Ohms Law. The signal representative of physiological impedance can vary with respiration of the subject to provide respiration information. The impedance sensor can therefore be used as a respiration sensor to measure respiration parameters such as respiratory rate, tidal volume, minute respiration volume, and derived parameters such as the ratio of respiratory rate over tidal volume. An approach to monitoring thoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference in its entirety.

The impedance signal from the impedance sensor can also provide information related to a change in fluid build-up in the thorax region of the subject. For instance, a DC or near DC component of the physiological impedance signal measured across the thorax region of the patient may be representative of fluid in trans-thoracic tissue. A decrease in the impedance may indicate an increase in fluid in cardiopulmonary vascular or interstitial space. Measurements made using different excitation parameters such as multiple frequencies can be used to separate the contribution of fluid from intracellular and extracellular compartments.

Intracardiac volumes may be derived from impedance measurements between different combination of electrodes such as, 116 to 114A and/or 114B, 118 to 120A and/or 120B, 120A/B to 128A/B, 118 to 128A and/or 128B, 119 to 128A and/or 128B, and 114A/B to 128A/B. Longer-term hematocrit (or hemoglobin) and plasma conductivity or its changes may be estimated for example by averaging blood pool impedance gated to specific periods in the cardiac cycle and averaged across 10 to 100 cardiac cycles for example, between electrodes 116 to 114A and/or 114B, or 116 to 119A and/or 119B.

Ambulatory medical devices can sense other types of physiological signals. For instance, an ambulatory medical device may include an activity sensor such as an accelerometer to sense physical motion of the patient (e.g., by filtering an accelerometer signal). In another example, ambulatory medical devices can provide heart sound sensing. An ambulatory medical device may sense heart sounds with the same accelerometer used to sense physical motion by sensing the accelerometer signal differently. In other examples cardiac vibrations may be sensed by an accelerometer integrated with the RV lead or the LV lead. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the closing of the aortic valve and the beginning of diastole. The third heart sound (S3) and fourth heart sound (S4) are related to filling pressures of the left ventricle during diastole. A heart sound sensor generates an electrical heart sound signal which is representative of mechanical cardiac activation of subject. Some examples of a heart sound sensor include an accelerometer and a microphone. An approach for monitoring heart sounds is described in Siejko et al., U.S. Pat. No. 7,972,275, "Method and Apparatus for Monitoring of Diastolic Hemodynamics," filed Dec. 30, 2002, which is incorporated herein by reference in its entirety.

Other sensors that may be used in implanted devices may produce measurements of pressures in various regions of the body including the circulation, biochemistry in various fluid compartments/spaces (such as vascular, interstitial, intraperitoneal), and electrical activity in sensory and motor neurons. Impedance in various tissue spaces such as the lead tip electrodes, and the subcutaneous PG pocket (for example from electrodes located on the header 107 to the can) may be used to estimate local interstitial tissue conductivity and sodium concentration. A variety of sensors such as bioimpedance electrodes, accelerometers, thermistors or thermocouples, light emitting diodes and photodiodes may be integrated in to the body of the device 105 or 107 or on leads 110, 115, 125 to measure physiologic parameters.

Combinations of such sensors can also be useful. For instance, a combination of an activity sensor with one or both of a respiration sensor and a heart rate sensor is useful for monitoring a patient's physiological response to activity (PRA), such as to detect deviations in one or both of breathing and reflex sympathetic activation due to activity. Alternatively, changes in the relationship of the volume index to patient activity levels measured during activities of daily living can allow the detection of early deviations in volume status that are not apparent at rest. In another example, a combination of heart sound sensing and electrogram sensing allow for measurements of time intervals from a fiducial in a first sensor signal to a fiducial in a second sensor signal. For instance, sensing both heart sounds and electrograms allows for monitoring the systolic time interval (STI). STI is the time interval measured from the beginning of the QRS complex to the first (aortic) vibration of the S2 heart sound. Other examples of implantable sensors include a temperature sensor, an ultrasound velocity sensor, an impedance sensor, and an optical spectrometry sensor.

In other examples, the implanted device may integrate information from external sensors such as weight, blood pressure, patient symptom self-assessments, and point-of-care measurements of blood chemistry biomarkers (such as NPs, creatinine, BUN, troponin, galectin-3, troponin, ST2 related markers, procalcitonin, neutrophil gelatinase-associated lipocalin, kidney injury molecule, plasma electrolytes), ultrasonography (lung comets, E/E' ratio, acoustic tissue velocity, vessel/cardiac dimensions), RF impedance (lung water measurement), and optical spectrometry (oximetry and cutaneous blood flow). In further examples, the implanted device may integrate temperature information from a temperature sensor, velocity information from an ultrasound sensor, and spectrum information from optical spectrometry.

These sensing functions provided by ambulatory medical devices may have utility for HF monitoring. Indications from multiple sensors can be combined into an accurate volume index without the need to prescribe a dedicated PA pressure sensing device for the patient. The volume index can allow the fluid status of the patient to be managed to a optivolemic range. Additionally, device-based analysis of the sensed patient condition can lead to recommendations from the device on adjusting a therapy. If the patient is prescribed a drug-based therapy, the device can make recommendations to changes in one or both of the drug-based therapy and a device-based therapy. In other examples, the device can automatically alter a therapy using a closed-loop control system with or without user assistance.

Figure 2:
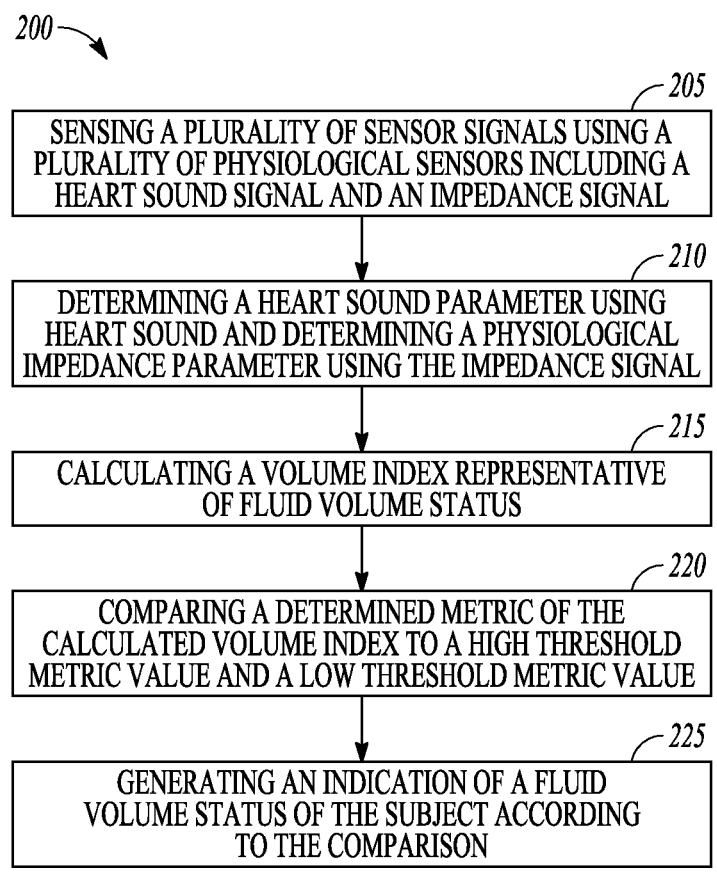
FIG. 2 shows a flow diagram of a method of controlling operation of an ambulatory medical device.

FIG. 2 shows a flow diagram of a method 200 of controlling operation of an ambulatory medical device. At 205, multiple sensor signals are sensed using multiple physiological sensors. The multiple sensor signals can include a heart sound signal and an impedance signal.

At 210, a value of at least one heart sound parameter is determined using the heart sound signal. Some examples of heart sound parameters include the amplitude of an S3 heart sound and the amplitude of the S1 heart sound. A value of at least one physiological impedance parameter can be determined using the impedance signal. An example of a physiological impedance parameter includes a respiration parameter such as tidal volume or respiration rate. Another example includes an impedance value representative of fluid in tissue of the thorax region of the subject.

At 215, a volume index representative of fluid volume status of the subject is calculated using one or more heart sound parameter values and one or more physiological impedance parameter values. In some examples, the volume index is a linear combination of the heart sound parameter and the respiration parameter, such as $$\text{Index} = a^*(\text{heart sound parameter}) + b^*(\text{physiological impedance parameter}),$$

where a and b can be constants determined from tuning the index to optimize accuracy of fluid volume status of a patient.

Because no single volume measurement is perfect, the volume index may be derived by not only using multiple sensors, but also using multiple volume measures for a given patient. The sensor outputs and the volume measures can be combined to derive a more accurate equation that describes the volumes status of the patient.

The inputs that are used to calculate the volume index and its resulting outputs may be mathematically transformed, and filtered to reduce the random day to day fluctuations. Transformation methods may include logarithms and power transforms and normalization using other measurements (for example, ratios of sensor measurements based on specific body postures, or time of day, or one sensor vs. another). Filtering can be used to emphasize changes in specific time frames. Smoothing may be used to remove random "short term" variations in the signal (example, with a time constant of minutes to days). Additionally, filtering may be applied with time constants of weeks, months, and years to extract moderate to long-term changes in signals. A combination of absolute volume index and relative changes (e.g., from a baseline) may be used to either adjust therapy in the short or long-term. Some examples of short-term changes include adjusting intravenous diuretic infusion or ultrafiltration rates during an in hospital stay, adjustment of oral diuretics in an ambulatory setting, adjustment of intravenous fluid infusion rate, and CRT optimization. Changes in volume index in response to diuretic therapy may be used to determine the diuretic responsiveness of the patient and to initiate changes in class of diuretic used. Additionally, short term volume index signals may be used to alert the clinician to prevent the acute worsening of heart failure. Some examples of long-term adjustments include therapy to improve patient prognosis over several months to years. These include changes to CRT device programming, optimization of drug dosage such as beta-blockers, ACEI, ARBs, and angiotensin receptor-neprilysin inhibitor, and inotropes. Another example is the indication for cardiac ablation, renal ablation therapy, autonomic modulation therapy.

Other applications possible with volume index measurements include differential diagnosis of the factors responsible for a hospitalization or worsening disease episode, the need treat a patient in an inpatient or outpatient setting, gradual adjustment of therapy intensity to restore the optivolemic state, patient discharge readiness from an inpatient admission, adjustment of patient treatment during transitions of care (for example, from hospital to home), treatment adjustment in the patient's "vulnerable period" following discharge from a hospital, need for ventricular assist therapy, need for regenerative, therapy need for heart transplant, or transition to palliative care.

Some examples of filters for inputs to the volume index include linear filters (finite or infinite impulse response) or non-linear filters. For instance, these examples can include a moving average (mean), a median, a alpha-trimmed mean, or spline filters. Short term changes can be compared to the long-term reference value to calculate changes in the signal. Further, the morphology of volume signals in different time-frames may be used to classify patients and their disease status in to relatively homogeneous groups (clusters) that facilitate better treatment and outcomes.

At 220, a metric of the calculated volume index is compared to a high threshold metric value and a low threshold metric value. In certain examples, the metric is the volume index and the volume index is compared to a high threshold index value (hypervolemic index) and a low threshold index value (hypovolemic index). In certain variations, the metric is a change in the volume index (e.g., from a calculated baseline index value), and the change in the index value is compared to a high threshold index change value and a low threshold index change value.

In some variations, the metric is the change or the rate of change of the volume index. The rate of change may be calculated as the ratio of the change in value of the volume index over the duration of time that the change in value occurred. The rate of change of the volume index is compared to a high threshold rate of change value and a low threshold rate of change value. In certain variations, the metric is the variability of volume index values. Variability of the volume index can be determined by calculating the change between values of the volume index, or the difference between successive values of volume index. In some variations, variability is calculated as a value of variance, standard deviation, interquartile range, mean absolute deviation, or root mean square deviation of the values of the volume index. The variability of the calculated volume index is compared to a high threshold variability value and a low threshold variability value.

At 225, an indication of a fluid volume status of the subject is generated according to the comparison. The indication may be a signal communicated to a process to generate a recommendation from the device on adjusting a therapy, or the indication can be communicated to a process to alter device-based therapy. Because the metric of the volume index is compared to high and low threshold values, both hypervolemia and hypovolemia of the subject can be detected and the indication can be used to make changes to correct for both conditions.

Figure 3:
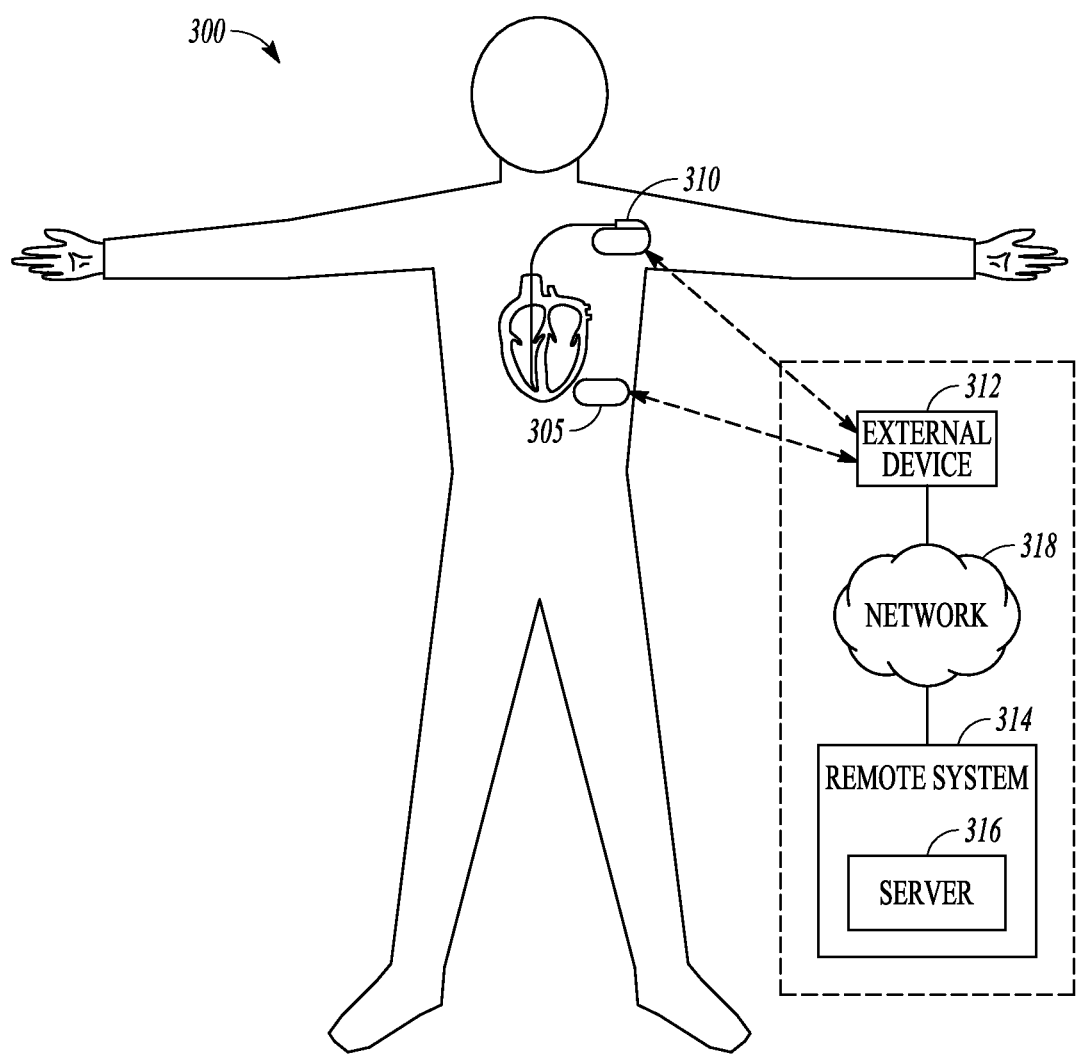
FIG. 3 shows an example of a medical device system.

FIG. 3 shows an example of a medical device system 300. The system 300 includes an ambulatory device for monitoring effects of dosing of an HF subject. The ambulatory device can be a wearable device 305, such as a patch or vest that monitors one or more physiological parameters of the subject for example. The wearable device 305 may be incorporated into an article of clothing or may be adherable to the subject's skin. The ambulatory device can be an IMD 310, such as a pacemaker or implantable cardioverter/defibrillator (ICD, e.g., transvenous ICD or subcutaneous ICD) that provides electrical therapy to the HF subject. In certain examples, the IMB 310 can include a drug reservoir to provide a drug therapy to the HF patient, or the IMB 310 can be a monitoring device used only for diagnostic purposes. In some examples, the medical device system 300 includes both the IMD 310 and the wearable device 305. The combination may be desirable based on the types of sensing desired. For instance, certain types of physiological parameters may be advantageously sensed using an implantable device and other types may be more advantageously sensed with a wearable device.

The medical device system 300 can include an external communication device 312 to communicate with the ambulatory medical device and with any external sensing devices. The communication may be wireless using wireless telemetry. The external communication device 312 may communicate with a remote system 314 via a network 318 (e.g., the internet, a proprietary computer network, or a cellular phone network). The remote system 314 may include a server 316 remotely located from the external communication device 312 and the HF subject to perform patient management functions, such as accessing electronic medical records (EMRs). The external communication device 312 may include a programmer to program therapy parameters of a device-based therapy provided by the ambulatory device. In certain examples, the external communication device 312 includes a repeater to communicate programming changes or other communication initiated by the remote system 314. The term repeater refers to a communication device local to the patient to relay communication signals between the remote system 314 and the medical device system 300.

The medical device system 300 may also include communication among various implantable intra-body sensors that form a communication network. The intra-body communication can provide various measures such as renal function or abdominal pressure to the IMD 310. An approach to intra-body medical device communication can be found in Vallapureddy et al., U.S. Pat. No. 7,743,151, "System and Method for Providing Digital Communications Over a Wireless Intra-Body network," filed Aug. 5, 2004, which is incorporated herein by reference in its entirety.

In some examples, patient covariate information can be included in calculation of the index. The covariate information may be available in electronic medical records (EMRs). In variations, this information may reside on server 316 or may be accessed by the server 316. The covariate information can include patient demographic information, disease history and comorbidity information. Demographic measures include the age of the patient, race, weight, height, body mass index (BMI), chest circumference, waist circumference, adiposity measures, lean body mass, etc. Disease history in HF patients include etiology such as ischemic/non-ischemic disease, cardiomyopathy type (dilated cardiomyopathy), cardiac dimensions, LV and RV ejection fraction, atrial and ventricular arrhythmia, valve surgery, coronary artery bypass graft surgery, artificial valve implants and other structural interventions. Comorbidity information in HF patients include patient's history of hypertension, diabetes, renal disease, chronic obstructive pulmonary disease, anemia, liver disease, sleep disordered breathing, gout, etc. The medical device system 300 may provide for monitoring fluid status of the patient by calculating the volume index using one or both of the sensor information and the covariate information.

The comorbidity information may be available in electronic medical records or entered by the user into the external device. The user may enter the covariate information directly or its component values with the calculation done by the processor 605. BMI can be entered directly or as its components of weight and height. Similarly, eGFR can be entered directly, or a serum creatinine value (SCr) can be entered and a number of different equations known in the art can be used by the system, such as the Cockcroft-Gault, Modification of Diet in Renal Disease (MDRD), or the CKD-EPI (Chronic Kidney Disease Epidemiology) to calculate eGFR. Weight, age, gender, and race can be entered and used to determine eGFR. The comorbidity information can be included directly into calculation of the volume index or can be used to change the importance of other measured parameter in the volume index, such as by weighing measured parameters differently in the presence of a comorbidity for example. The medical device system 300 may provide for monitoring fluid status of the patient by calculating the volume index using one or more of the sensor information, the covariate information, and the comorbidity information. In some examples, a sensor measured value can be removed from the volume index when use of the sensor is counter-indicated by the comorbidity information.

Figure 4:
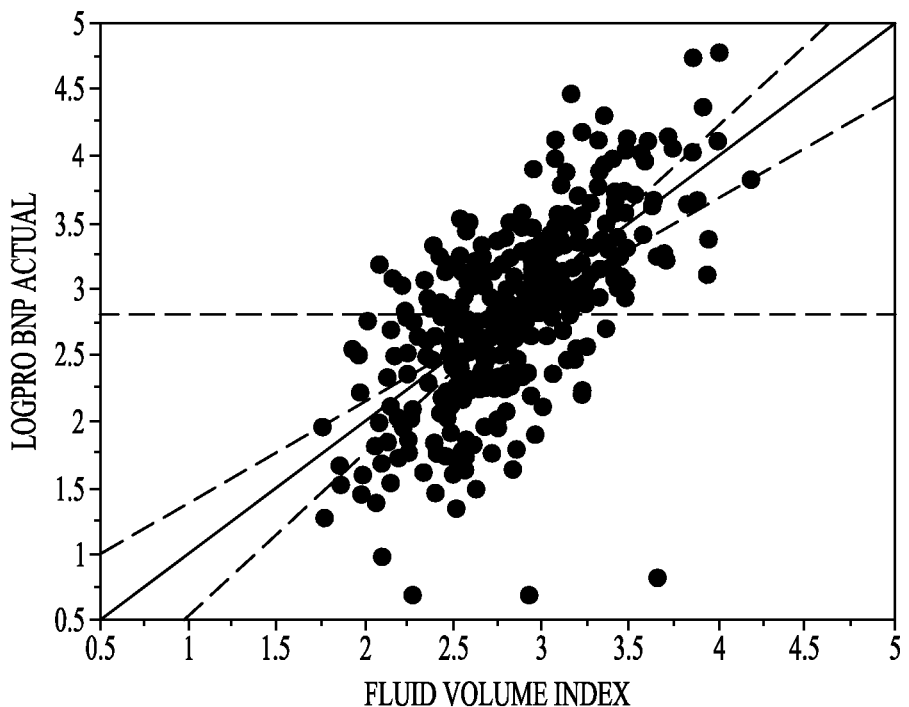
FIG. 4 shows a graph or plot of an example of patient data.

FIG. 4 shows a graph or plot of patient data. The vertical axis is the value of the measured NT-proBNP biomarker and the horizontal axis is a calculated fluid volume index. The volume index was calculated as a linear combination of covariate information and sensor information. The covariate information included a patient's age, a patient's BMI and a value of a patient's eGFR (e.g., estimated using the CKD-EPI equation). The sensor information included a value of the amplitude of the S3 heart sound, a value of impedance measured from the right ventricle to an electrode included on a can of an IMD of a patient, a value of the amplitude of the S1 heart sound, a value of an STI, a value of tidal volume (TV). The patient data was averaged over a first week. FIG. 4 compares NT-ProBNP to the volume index predicted by the model. The correlation coefficient which represents the linear dependence between the volume index and the NT-proBNP value was 0.66 (r-squared=0.44). The r-squared value is almost 3-fold greater than any single input parameter of the model indicating that there was significant benefit to combining input variables to estimate NT-proBNP. The model tested one year after patient follow-up demonstrated an unchanged r-squared value indicating that the model was stable.

Figure 5:
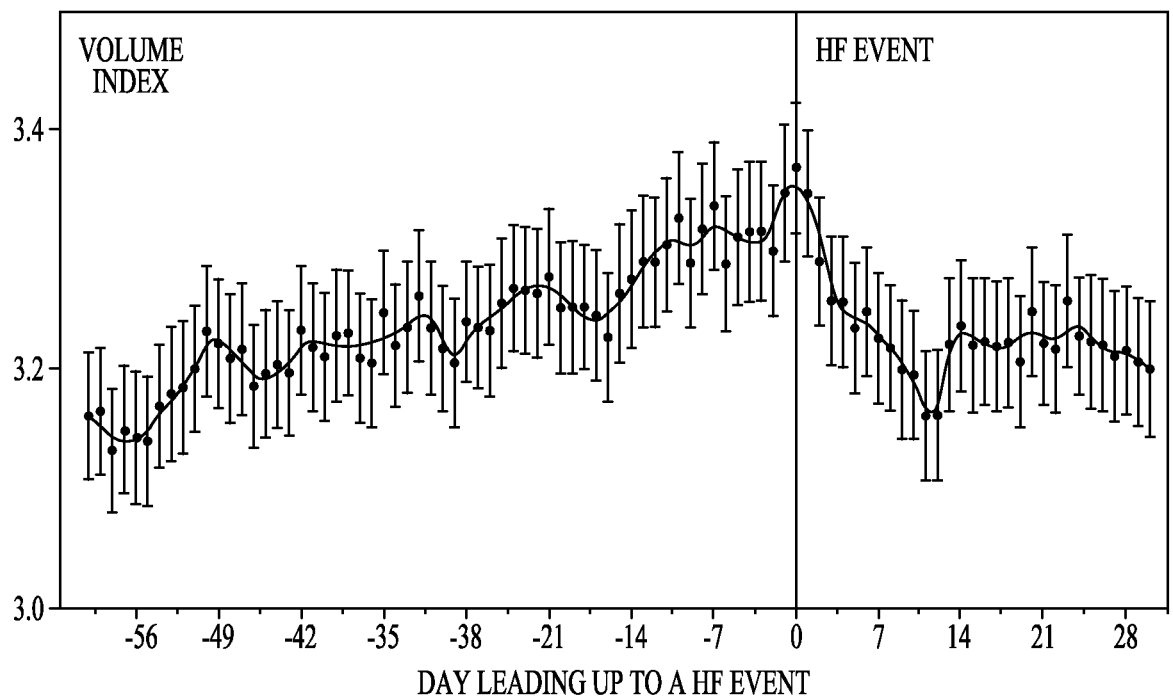
FIG. 5 shows a plot for values of a volume index leading up to a heart failure event.

FIG. 5 shows a plot for the average volume index leading up to a heart failure event demonstrating an increase in volume prior to worsening HF. This is consistent with finding that the vast majority of worsening HF events is associated with signs and symptoms of fluid volume overload.

Figure 6:
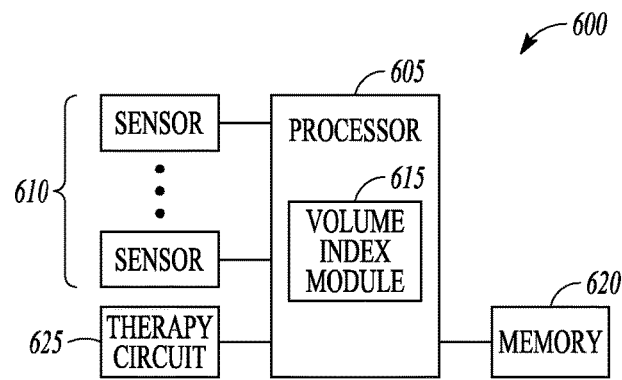
FIG. 6 is a block diagram of an example of portions of a device to monitor fluid volume status.

FIG. 6 is a block diagram of an example of portions of a device 600 to monitor fluid volume status of a patient or subject. The device 600 includes multiple sensors 610. Each of the sensors 610 provides a sensor signal that includes physiological information. The multiple sensors 610 include a heart sound sensor that generates a heart sound signal representative of mechanical cardiac activation of a subject, and an impedance sensor that generates an impedance signal representative of physiological impedance of the subject. In certain examples, one or both of the heart sound sensor and the impedance sensor are implantable. In certain examples, the multiple sensors include an electrogram sensing circuit.

The device 600 includes a processor circuit 605 communicatively coupled to the multiple sensors 610. The communicative coupling allows the processor circuit 605 and the sensors 610 to communicate even though there may be intervening circuitry between the processor circuit 605 and the sensors 610. The processor circuit 605 may include a microprocessor, a digital signal processor, application specific integrated circuit (ASIC), microprocessor, or other type of processor, interpreting or executing instructions in software or firmware. The processor circuit 605 can include modules to perform the functions described. Modules can be software, hardware, firmware or any combination thereof. Multiple functions can be performed in one or more modules as desired.

The processor circuit 605 includes a volume index module 615. The volume index module 615 determines a value of at least one heart sound parameter using the heart sound signal and determines a value of at least one physiological impedance parameter value using the impedance signal. An example of a heart sound parameter includes the amplitude of a heart sound (e.g., the S1 heart sound or the S3 heart sound) in the heart sound signal. An example of a physiological impedance parameter includes an impedance representative of the level of tissue fluid of the subject (e.g., interstitial fluid or fluid in the thorax region), and a respiration parameter (e.g., respiratory tidal volume) extracted from the impedance signal.

In certain examples, the volume index module 615 calculates the validity of a heart sound signal or an impedance signal based on known characteristics of the signal in the patient population such as the absolute value, standard deviation (variation), and signal morphology (e.g., step changes, impulse noise, etc.). If the signal is deemed to be valid, the volume index module 615 calculates a volume index representative of fluid volume status of the subject using one or more heart sound parameter values and one or more physiological impedance parameter values.

In some examples, the device 600 includes a memory 620 that stores eGFR information and BMI information of the subject. The volume index module 615 calculates the volume index using the at least one heart sound parameter value, the at least one physiological impedance parameter value, the eGFR information, and the BMI information. The volume index module 615 may calculate the volume index as a linear combination of the at least one heart sound parameter value, the at least one respiration parameter value, a value of eGFR, and a value of BMI. In certain examples, the volume index module 615 calculates the volume index as a non-linear combination of the parameter values and covariate information. In some examples, the volume index module 615 calculates the volume index of fluid volume status using at least one of a value of intracardiac impedance, a value of a systolic time interval (STI), and age of the subject. In some examples, the volume index is a linear combination of one or more heart sound parameter values, one or more respiration parameter values, the value of eGFR, the value of BMI, the value of intracardiac impedance, the value of STI, and the age of the subject. In certain examples, the volume index is calculated as Index=a*(S3 amplitude)+b*(S1 amplitude)+c*(eGFR)+d*(BMI)+e*(age in years)+f*(Impedance of RV to can)+g*(STI)+h*(tidal volume).

More than one set of models and coefficients may be stored in memory. In certain examples, the volume index module 615 determines if the volume index can be accurately determined from the available inputs. For instance, sensor measurements may be invalid due to replacement or repositioning of one or both of a device or a device lead.

Invalidity may be determined automatically from detecting non-physiologic changes in IMB sensor outputs (such as step changes in the signal or impulses) or from user input. If the volume index can be accurately calculated using the available variables, the volume index module 615 selects an appropriate model based on the available data.

The volume index module 615 compares a metric related to the volume index to a high threshold metric value and a low threshold metric value. In certain examples, the volume index module 615 compares the calculated volume index to a high threshold index value and a low threshold index value. In certain examples, the volume index module 615 determines the rate of change of the calculated volume index and compares the determined rate of change to a high threshold rate of change value and a low threshold rate of change value. In certain examples, the volume index module 615 determines the variability of the calculated volume index and compares the determined variability to a high threshold variability value and a low threshold variability value. In certain examples, the volume index module 615 calculates one or more of the volume index metrics stated above and compares it to two or more high threshold values and two or more low threshold values.

In order to determine if the patient requires an intervention, the volume index module 615 may derive the appropriate metric from the volume index signal, and calculates the hypervolemic and hypovolemic thresholds. Because the optivolemic range may change over time as a result of disease progression this range may need to be adjusted for a given patient. In one example, the upper and lower thresholds may be determined automatically from signal changes after filtering using moderate or long-term time constants. The time frames when the patient was in a stable optivolemic state may be identified automatically, with clinician or patient assessment, or a combination of the above. Clinician inputs may be entered in to the volume index processor at patient follow-ups or remotely along with covariate information. In certain examples, changes in volume index associated with patient symptoms and clinical events are used to determine the optivolemic range. In certain examples, the clinician or patient may enter a subjective assessment of congestion at each follow-up for example, every 3 months and the volume index may be compared to this metric to determine the optivolemic range. In certain examples, treatment may be carefully and gradually withdrawn or increased by the clinician to identify the optivolemic range. In certain examples, a progressive decline in the optivolemic range may be used to recommend ventricular assist therapy, regenerative therapy, or organ transplant.

The volume index module 615 generates an indication of a fluid volume status of the subject according to the comparison to the high and low thresholds. The generated indication may be an electrical signal communicated to a process executing on the processor circuit 605 or a different processor circuit. In certain examples, the device 600 includes a display. The indication of the fluid volume status may be presented to a user via the display. As explained previously herein, both hypervolemia and hypovolemia of the subject can be detected because the metric of the volume index is compared to high and low threshold values. The processor circuit 605 generates an indication of a change to a treatment for at least one of hypervolemia or hypovolemia of the subject according to the generated indication of fluid volume status.

In some examples, the device 600 includes a therapy circuit 625 that controls a device-based therapy to the subject. Based on the generated indication of fluid status, the processor circuit 605 changes a parameter of the device-based therapy to lower the determined metric of the calculated volume index to a value less than the high threshold metric value and increase the determined metric of the calculated volume index to a value greater than the low threshold metric value. In certain examples, the device-based therapy includes at least one of pacing therapy, cardiac resynchronization therapy (CRT), defibrillation therapy, autonomic modulation therapy, and left ventricular assist therapy. The processor circuit 605 changes a parameter of one or more of pacing therapy, cardiac resynchronization therapy (CRT), defibrillation therapy, autonomic modulation therapy, fluid removal therapy, fluid infusion therapy, ultra-filtration therapy, drug delivery therapy, or left ventricular assist therapy to either lower or raise the volume index to a specified range according to the generated indication. In certain examples, the device-based therapy includes device-based drug therapy, and the processor circuit 605 changes a parameter related to dosing of the subject according to the generated indication. In certain examples, the processor circuit 605 generates an alert when the volume index is outside the threshold metric values. The alert can be provided to a process or a user. The patient may be prescribed to change an oral drug (such as a diuretic) in response to an alert. The drug dosage information may be transmitted to the system from an automated pill box or with pill identification (example, optical or RF ID) and the subsequent change in volume index divided by the drug dosage may be used to estimate drug responsiveness and efficacy. Drug responsiveness may be trended over time in patients and used to change prescriptions manually or automatically with or without clinician verification.

Figure 7:
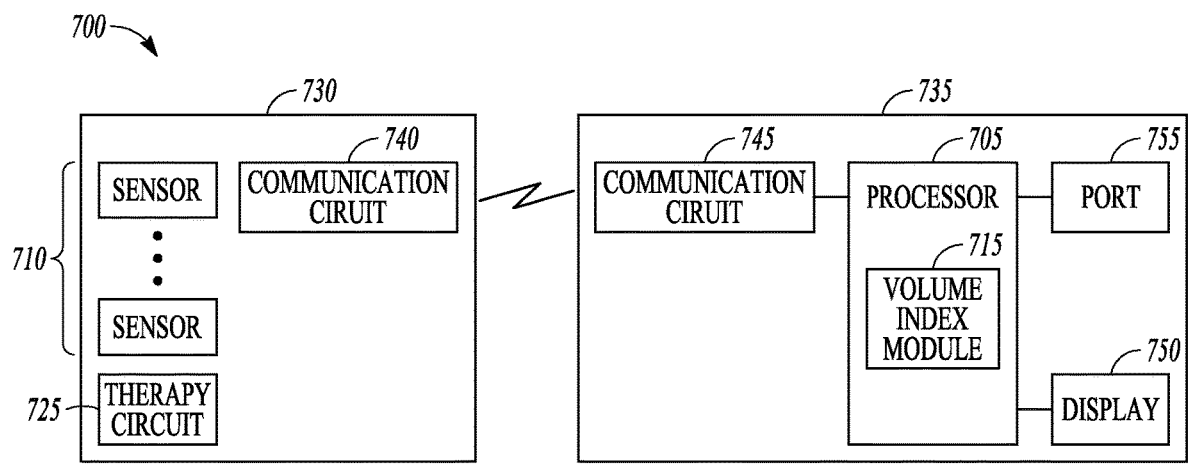
FIG. 7 is a block diagram of an example of portions of a system to monitor fluid volume status.

FIG. 7 is a block diagram of an example of portions of a system 700 to monitor fluid volume status of a patient or subject. The system 700 includes an ambulatory medical device 730 and a second device 735. The ambulatory medical device 730 maybe any of the examples of ambulatory devices described herein, such as an implantable device or a wearable device. Some examples of the second device 735 include a programmer, a server, repeater or any combination of a programmer, a server, and repeater.

The ambulatory medical device 730 includes a plurality of physiologic sensors 710. The sensors may include a heart sound sensor that generates a heart sound signal representative of mechanical cardiac activation of a subject, and a respiration sensor that generates a respiration signal representative of respiration of the subject. In certain examples, the respiration signal is a sensed impedance signal. The ambulatory medical device 730 also includes a communication circuit 740 that communicates information with the second device 735. The second device 735 includes a second communication circuit 745 that communicates information with the ambulatory medical device 730. The second device 735 also includes a display 750 and a processor circuit 705. The processor circuit 705 includes a volume index module 715 that determines a value of at least one heart sound parameter using the heart sound signal, determines a value of at least one respiration parameter using the respiration signal, and calculates a volume index representative of fluid volume status of the subject using the at least one heart sound parameter value and the at least one respiration parameter value. In some examples, the volume index module uses one or both of covariate information and comorbidity information when determining the volume index.

The volume index module 715 compares a metric related to the volume index to a high threshold metric value and a low threshold metric value as explained previously herein and generates an indication of a fluid volume status of the subject according to the comparison. The processor circuit 705 displays a recommended change to a treatment for one or both of hypervolemia and hypovolemia of the subject according to the comparison. In certain examples, the processor circuit 705 displays a recommended change to one or more treatments for the patient's disease such as, a pacing treatment, a defibrillation treatment, ventricular assist device treatment (such as an LVAD, RVAD, or a total artificial heart), ablation treatment, a neuromodulation treatment, drug delivery treatment (drug pump/reservoir), an ultrafiltration treatment, a structural heart treatment, a chronic IV treatment schedule, or an oral pharmacological treatment schedule. In certain examples, the processor circuit 705 automatically adjusts one or more of the pacing treatment, defibrillation treatment, ventricular assist device treatment, ablation treatment, neuromodulation treatment, drug delivery treatment, ultrafiltration treatment, dialysis treatment, the chronic IV treatment, or the pharmacological treatment in response to the generated indication of fluid volume status.

In some examples, the ambulatory medical device 730 includes a therapy circuit 725 configured to control a device-based therapy provided to the subject. The processor circuit 705 determines, according to the comparison of the calculated volume index, a value of a parameter of the device-based therapy to move the volume index toward a volume index target value and communicates the value of the parameter to the ambulatory medical device 730.

As explained previously herein, the volume index follows the actual NT-proBNP volume biomarker well enough for the volume index to be a monitor for patient fluid volume. According to some examples, the volume index can be made tunable to improve the matching to multiple volume biomarkers, other than the NT-proBNP volume biomarker (e.g., a vascular fluid volume biomarker such as hemoglobin or total protein, or other biomarker, such as sST2 renal biomarkers, or external biomarkers such as lung comets). The second device 735 may include a port 755 to receive fluid volume marker information. In certain variations the port 755 is a communication port or COMM Port, and the fluid volume biomarker information is received from a second device. In certain variations, the port 755 communicatively coupled to a user interface and the fluid volume biomarker information is received from a user.

The processor circuit 705 may adjust the method of calculating the volume index according to the fluid volume biomarker information received via the port 755. For instance, if the volume index is calculated as a linear combination of measured sensor values and covariate information, the processor circuit 705 may tune the calculation of the volume index to better match the volume biomarker information by changing one or more of the constants used to modify the sensor values and covariate information. For instance, a clinician may periodically (e.g., every six months) enter an NT-proBNP value for the patient into the system, and volume index module may run a least squares fit to calculate the model coefficients (e.g., coefficients a-h in the Index equation described previously). In another example, the processor circuit 705 adjusts a weighting applied to one or more of the sensor values and covariate information. The weighting can be adjusted to zero to remove one or more of a sensor output, specified covariate information, and specified comorbidity information from the volume index calculation. In some examples, the method of calculating the volume index is changed according to the received fluid volume biomarker information. For example, the processor circuit 705 may change the calculating of the volume index by the volume index module 715 from using a linear combination of values to using a non-linear combination of values.

The availability of a volume index may enable the system 700 to report how some measurements (such as heart rate, weight, respiration rate, neural activity) are related to volume changes in the body. Similarly patient volume index changes leading up to clinical events (such as worsening HF) may allow better characterization and treatment of the patient's disease. In certain examples, patient discharge following a worsening HF hospitalization may be determined by the volume index at discharge compared to the dynamic changes occurring before and during admission.

Due to the heterogeneity with which fluid is distributed in the body, the total body volume index may be split into regional volume indices for body regions where volume is known to accumulate. Implanted and external sensors that measure physiological parameters associated with volume in these regions may be used to derive a regional volume index. In certain examples, a regional volume index may be derived for the thorax to measure central congestion. Similarly, a regional volume index may be derived for fluid accumulation in the dependent regions of the body where gravity causes fluid to accumulate (such as the limbs or abdomen). In another example, a subcutaneous diagnostic may measure the fluid in the interstitial space compared to another sensor located in the vascular space. Similarly, the relative distribution of fluid in the extracellular vs. intracellular spaces may be derived from multi-frequency impedance measurements that may be used with other parameters to derive regional volume indices. The distribution of fluid as measured by regional volume indices may be used to adjust therapy for the patient. In certain examples, the relative contributions of central and peripheral volume indices leading to weight gain and worsening HF may be used to adjust the type and intensity of therapies to bring the patient back to a optivolemic state.

The volume marker information may be obtained from a patient population and the volume index can be tuned to the patient population volume biomarker. Due to the known heterogeneity in the nature of the disease state and the resulting interventions, patients are typically grouped into clusters using patient characteristics such as demographics, heart failure etiology, cardiac disease history, comorbidities, and biomarkers. With the availability of implanted sensor readings and volume index, cluster membership may be determined using volume index changes leading to clinical events, or alternatively from volume changes in response to interventions.

In certain examples, patient membership in a group may be determined from the change in volume to gradual withdrawal of medications. In more examples, group membership may be determined from the morphology of changes in volume index leading to a worsening HF event and patient/event characteristics (acuity of symptoms, length of admission, worsening of comorbidities). Other examples of interventions used for patient clustering include changes in body posture (measured either from activities of daily living or due to a planned intervention), Valsalva or Mueller maneuvers, activity, time of day, and various therapies (such as fluid infusion).

The volume marker information can be for a specific patient, and the volume index can be tuned to better match the fluid volume marker for the individual patient. Thus, the monitoring by an ambulatory device prescribed to an individual can be optimized for that individual patient. The device-based monitoring can provide continuous or near-continuous monitoring of the condition of the patient.

ADDITIONAL DESCRIPTION AND EXAMPLES

Example 1 can include subject matter (such as an apparatus) comprising a plurality of physiologic sensors, including a heart sound sensor configured to generate a heart sound signal representative of mechanical cardiac activation of a subject and an impedance sensor configured to generate an impedance signal representative of physiological impedance of the subject; and a processor circuit communicatively coupled to the plurality of physiologic sensors. The processor circuit includes a volume index module configured to: determine a value of at least one heart sound parameter using the heart sound signal and determine a value of at least one physiological impedance parameter value using the impedance signal; calculate a volume index representative of fluid volume status of the subject using the at least one heart sound parameter value and the at least one physiological impedance parameter value; compare a determined metric of the calculated volume index to one or more high threshold metric values and one or more low threshold metric values; and generate an indication of a fluid volume status of the subject according to the comparison.

In Example 2, the subject matter of Example 1 optionally includes a processor circuit configured to generate an indication of a change to a treatment for at least one of hypervolemia or hypovolemia of the subject according to the generated indication of fluid volume status.

In Example 3, the subject matter of one or both of Examples 1 and 2 optionally includes a memory configured to store patient-specific body measurements, disease information, and comorbidity information, wherein the volume index module is optionally configured to calculate the volume using the at least one heart sound parameter value, the at least one physiological impedance parameter value, and the patient disease and comorbidity information.

In Example 4, the subject matter of one or any combination of Examples 1-3 optionally includes a memory configured to store estimated glomerular filtration rate (eGFR) information and body mass index (BMI) information of the subject; wherein the volume index module is optionally configured to calculate the volume index using the at least one heart sound parameter value, the at least one physiological impedance parameter value, the eGFR information, and the BMI information.

In Example 5, the subject matter of Example 4 optionally includes a volume index module configured to calculate the volume index using a linear combination of the at least one heart sound parameter value, the at least one respiration parameter value, a value of eGFR, and a value of BMI.

In Example 6, the subject matter of one or both of Examples 4 and 5 optionally includes an impedance sensor configured to generate a respiration signal representative of respiration of the subject, wherein the least one physiological impedance parameter value includes a value of respiratory tidal volume of the subject, and the at least one heart sound parameter includes at least one of a value of S3 heart sound amplitude and a value of S1 heart sound amplitude.

In Example 7, the subject matter of one or any combination of Examples 4-6 optionally includes a volume index module configured to calculate the volume index using at least one of: a value of intracardiac impedance; a value of a systolic time interval (STI); and age of the subject.

In Example 8, the subject matter of one or any combination of Examples 1-7 optionally includes a therapy circuit configured to control a device-based therapy to the subject, wherein the processor circuit is configured to change, according to the indication of fluid status, a parameter of the device-based therapy to lower the determined metric of the calculated volume index to a value less than the high threshold metric value and increase the determined metric of the calculated volume index to a value greater than the low threshold metric value.

In Example 9, the subject matter of one or any combination of Examples 1-8 optionally includes a therapy circuit configured to provide at least one of cardiac resynchronization therapy (CRT), drug therapy, fluid infusion therapy, autonomic modulation therapy, and left ventricular assist therapy.

In Example 10, the subject matter of one or any combination of Examples 1-9 optionally includes an impedance sensor configured to generate a respiration signal representative of respiration of the subject and wherein the at least one physiological impedance parameter includes one or both of tidal volume of the subject and respiration rate of the subject.

In Example 11, the subject matter of one or any combination of Examples 1-10 optionally includes an impedance sensor configured to generate a signal representative of at least one of: a tissue fluid level of the subject, hemoglobin level of the subject, or a hematocrit level of the subject.

In Example 12, the subject matter of one or any combination of Examples 1-11 optionally includes a volume index module configured to compare at least one of: the calculated volume index to a high threshold index value and a low threshold index value; a relative change in the volume index to high threshold index change value and a low threshold index change value; a rate of change of the calculated volume index to a high threshold rate of change value and a low threshold rate of change value; or a determined variability of the calculated volume index to a high threshold variability value and a low threshold variability value.

In Example 13, the subject matter of one or any combination of Examples 1-12 optionally includes a therapy circuit configured to control at least one of a device-based drug therapy, fluid removal therapy, or a fluid infusion therapy.

Example 14 can include subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-13 to include such subject matter, comprising: sensing a plurality of sensor signals using a plurality of physiological sensors, including a heart sound signal representative of mechanical cardiac activation of a subject and an impedance signal representative of physiological impedance of the subject; determining a value of at least one heart sound parameter using the heart sound signal and determining a value of at least one physiological impedance parameter value using the impedance signal; calculating a volume index representative of fluid volume status of the subject using the at least one heart sound parameter value and the at least one physiological impedance parameter value; comparing a metric of the calculated volume index to one or more high threshold metric values and one or more low threshold metric values; and generating, with the ambulatory medical device, an indication of a fluid volume status of the subject according to the comparison.

In Example 15, the subject matter of Example 14 optionally includes calculating the volume index of fluid volume status of the subject using estimated glomerular filtration rate (eGFR) information, body mass index (BMI) information, the at least one heart sound parameter value, and the at least one physiological impedance parameter value.

In Example 16, the subject matter of one or both of Example 14 and 15 optionally includes at least one of: comparing the calculated volume index to a high threshold index value and a low threshold index value; comparing a relative change in the volume index to high threshold index change value and a low threshold index change value; comparing a rate of change of the calculated volume index to a high threshold rate of change value and a low threshold rate of change value; or comparing a determined variability of the calculated volume index to a high threshold variability value and a low threshold variability value.

Example 17 can include subject matter (such as a system) or can optionally be combined with the subject matter of one or any combination of Examples 1-16 to include such subject matter, comprising an ambulatory medical device and a second device. The ambulatory medical device includes: a plurality of physiologic sensors, including a heart sound sensor configured to generate a heart sound signal representative of mechanical cardiac activation of a subject and a respiration sensor configured to generate a respiration signal representative of respiration of the subject; and a first communication circuit configured to communicate information with the second device. The second device includes: a second communication circuit configured to communicate information with the ambulatory medical device; a display; and a processor circuit. The processor circuit includes a volume index module configured to: determine a value of at least one heart sound parameter using the heart sound signal and determine a value of at least one respiration parameter using the respiration signal; calculate a volume index representative of fluid volume status of the subject using the at least one heart sound parameter value and the at least one respiration parameter value; and compare the calculated volume index to one or more high threshold index values and one or more low threshold index values, and wherein the processor circuit is configured to display a recommended change to a treatment for at least one of hypervolemia or hypovolemia of the subject according to the comparison.

In Example 18, the subject matter of Example 17 optionally includes a second device that includes a port configured to receive information from electronic medical records including estimated glomerular filtration rate (eGFR) information and body mass index (BMI) information, wherein the volume index module is configured to calculate the volume index of fluid volume status using the at least one heart sound parameter value, the at least one respiration parameter value, the eGFR information and the BMI information.

In Example 19, the subject matter of one or both of Examples 17 and 18 optionally includes a processor circuit of the second device is configured to display a recommended change to a pharmacological therapy.

In Example 20, the subject matter of one or any combination of Examples 17-19 optionally includes an ambulatory medical device includes a therapy circuit configured to control a device-based therapy to a subject, wherein the processor circuit of the second device is configured to determine, according to the comparison of the calculated volume index, a value of a parameter of the device-based therapy to move the volume index toward a volume index target value and communicate the value of the parameter to the ambulatory medical device.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    a plurality of physiologic sensors, including a heart sound sensor configured to generate a heart sound signal representative of mechanical cardiac activation of a subject and an impedance sensor configured to generate an impedance signal representative of physiological impedance of the subject; and
    a processor circuit communicatively coupled to the plurality of physiologic sensors, wherein the processor circuit includes a volume index module configured to:
    determine a value of at least one heart sound parameter using the heart sound signal and determine a value of at least one physiological impedance parameter value using the impedance signal;
    calculate a volume index representative of fluid volume status of the subject using the at least one heart sound parameter value and the at least one physiological impedance parameter value;
    compare a determined metric of the calculated volume index to one or more hypervolemia threshold metric values and to one or more hypovolemia threshold metric values; and
    generate an indication of a fluid volume status of the subject according to the comparison.

2. The apparatus of claim 1, wherein the processor circuit is configured to generate an indication of a change to a treatment for at least one of hypervolemia or hypovolemia of the subject according to the generated indication of fluid volume status.

3. The apparatus of claim 1, including a memory configured to store patient-specific body measurements, disease information, and comorbidity information, wherein the volume index module is configured to calculate the volume using the at least one heart sound parameter value, the at least one physiological impedance parameter value, and the patient disease and comorbidity information.

4. The apparatus of claim 1, including a memory configured to store estimated glomerular filtration rate (eGFR) information and body mass index (BMI) information of the subject; wherein the volume index module is configured to calculate the volume index using the at least one heart sound parameter value, the at least one physiological impedance parameter value, the eGFR information, and the BMI information.

5. The apparatus of claim 4, wherein the volume index module is configured to calculate the volume index using a linear combination of the at least one heart sound parameter value, the at least one respiration parameter value, a value of eGFR, and a value of BMI.

6. The apparatus of claim 4, wherein the impedance sensor is configured to generate a respiration signal representative of respiration of the subject, wherein the least one physiological impedance parameter value includes a value of respiratory tidal volume of the subject, and the at least one heart sound parameter includes at least one of a value of S3 heart sound amplitude and a value of S1 heart sound amplitude.

7. The apparatus of claim 4, wherein the volume index module is configured to calculate the volume index using at least one of: a value of intracardiac impedance; a value of a systolic time interval (STI); and age of the subject.

8. The apparatus of claim 1, including a therapy circuit configured to control a device-based therapy to the subject, wherein the processor circuit is configured to change, according to the indication of fluid status, a parameter of the device-based therapy to lower the determined metric of the calculated volume index to a value less than a high threshold metric value and increase the determined metric of the calculated volume index to a value greater than a low threshold metric value.

9. The apparatus of claim 8, wherein the therapy circuit is configured to provide at least one of cardiac resynchronization therapy (CRT), defibrillation therapy, drug therapy, fluid infusion therapy, autonomic modulation therapy, and left ventricular assist therapy.

10. The apparatus of claim 1, wherein the impedance sensor is configured to generate a respiration signal representative of respiration of the subject and wherein the at least one physiological impedance parameter includes one or both of tidal volume of the subject and respiration rate of the subject.

11. The apparatus of claim 1, wherein the impedance sensor is configured to generate a signal representative of at least one of tissue fluid level of the subject, a hemoglobin level of the subject, or a hematocrit level of the subject.

12. The apparatus of any one of claim 1, wherein the volume index module is configured to compare at least one of: the calculated volume index to a high threshold index value and a low threshold index value; a relative change in the volume index to a high threshold index change value and a low threshold index change value, a rate of change of the calculated volume index to a high threshold rate of change value and a low threshold rate of change value; or a determined variability of the calculated volume index to a high threshold variability value and a low threshold variability value.

13. The apparatus of claim 1, including a therapy circuit configured to control a device-based drug therapy, a fluid removal therapy, or a fluid infusion therapy.

14. A system comprising an ambulatory medical device and a second device, wherein the ambulatory medical device includes:
   a plurality of physiologic sensors, including a heart sound sensor configured to generate a heart sound signal representative of mechanical cardiac activation of a subject and a respiration sensor configured to generate a respiration signal representative of respiration of the subject; and
   a first communication circuit configured to communicate information with the second device;
wherein the second device includes:
   a second communication circuit configured to communicate information with the ambulatory medical device;
   a display; and
   a processor circuit including a volume index module configured to:
   determine a value of at least one heart sound parameter using the heart sound signal and determine a value of at least one respiration parameter using the respiration signal;
   calculate a volume index representative of fluid volume status of the subject using the at least one heart sound parameter value and the at least one respiration parameter value; and
   compare the calculated volume index to one or more hypervolemia threshold metric values and to one or more hypovolemia threshold metric values, and wherein the processor circuit is configured to display a recommended change to a treatment for at least one of hypervolemia or hypovolemia of the subject according to the comparison.

15. The system of claim 14, wherein the second device includes a port configured to receive information from electronic medical records including estimated glomerular filtration rate (eGFR) information and body mass index (BMI) information, wherein the volume index module is configured to calculate the volume index of fluid volume status using the at least one heart sound parameter value, the at least one respiration parameter value, the eGFR information and the BMI information.

16. The system of claim 14, wherein the ambulatory medical device includes a therapy circuit configured to control a device-based therapy to a subject, wherein the processor circuit of the second device is configured to determine, according to the comparison of the calculated volume index, a value of a parameter of the device-based therapy to move the volume index toward a volume index target value and communicate the value of the parameter to the ambulatory medical device.

* * * * *